United States Patent [19]

Silny et al.

[11] Patent Number: 5,109,870

[45] Date of Patent: May 5, 1992

[54] APPARATUS FOR AND METHOD OF MOTILITY AND PERISTALSIS MONITORING

[75] Inventors: Jiri Silny; Günter Rau, both of Aachen, Fed. Rep. of Germany

[73] Assignee: Forschungsgesellschaft fur Biomedizinische Technik e.V., Aachen, Fed. Rep. of Germany

[21] Appl. No.: 604,355

[22] Filed: Oct. 26, 1990

Related U.S. Application Data

[63] Continuation of Ser. No. 427,575, Oct. 23, 1989, abandoned.

[30] Foreign Application Priority Data

Oct. 25, 1988 [DE] Fed. Rep. of Germany ....... 3836349

[51] Int. Cl.⁵ .................................................. A61B 5/05
[52] U.S. Cl. ..................................... 128/780; 128/734; 128/642
[58] Field of Search ............... 128/642, 693, 734, 713, 128/780; 604/282, 270

[56] References Cited

U.S. PATENT DOCUMENTS

| | | | |
|---|---|---|---|
| 3,480,003 | 11/1969 | Crites | 128/780 |
| 4,073,287 | 2/1978 | Bradley et al. | 128/642 |
| 4,245,645 | 1/1981 | Arseneault et al. | 128/642 |
| 4,450,527 | 5/1984 | Sramek | 364/415 |
| 4,556,065 | 12/1985 | Hoffmann | 128/639 |
| 4,561,450 | 12/1985 | Bryant | 128/780 |
| 4,706,688 | 11/1987 | Michael et al. | 128/785 |
| 4,721,115 | 1/1988 | Owens | 128/713 |
| 4,836,214 | 6/1989 | Sramek | 128/693 |
| 4,887,610 | 12/1989 | Mittal | 128/733 |
| 4,898,176 | 2/1990 | Petre | 128/642 |
| 4,911,174 | 3/1990 | Pederson et al. | 128/695 |
| 4,960,133 | 10/1990 | Hewson | 128/784 |
| 5,025,786 | 6/1991 | Siegel | 128/642 |

Primary Examiner—William E. Kamm
Assistant Examiner—Kevin Pontius
Attorney, Agent, or Firm—Norman E. Brunell

[57] ABSTRACT

A catheter for measuring motility and peristalsis in tubular organs that transport their contents by simultaneous, multiple impedance measurements includes an insulating plastic tube, conductive annular electrodes and interior channels for electrode leads. The electrodes also serve for biosignal detection and electrical stimulation of the organ being measured. The interior channels may be used to stiffen the catheter during use, remove sample materials from the organ for analysis and/or introduce substances to the organ such as a contrast medium.

8 Claims, 4 Drawing Sheets

FIG. 6
FIG. 6 (a)
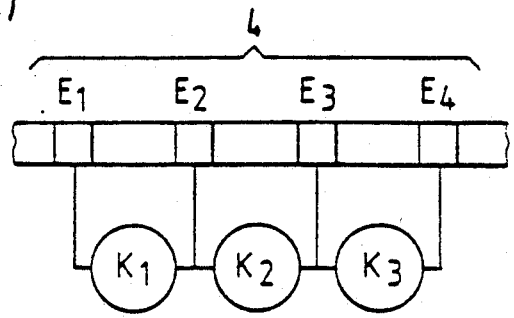
FIG. 6 (b)
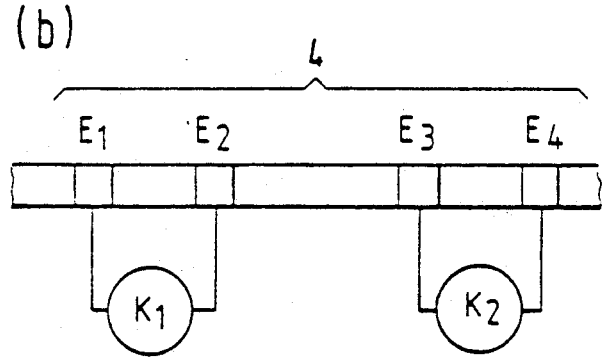
FIG. 6 (c)
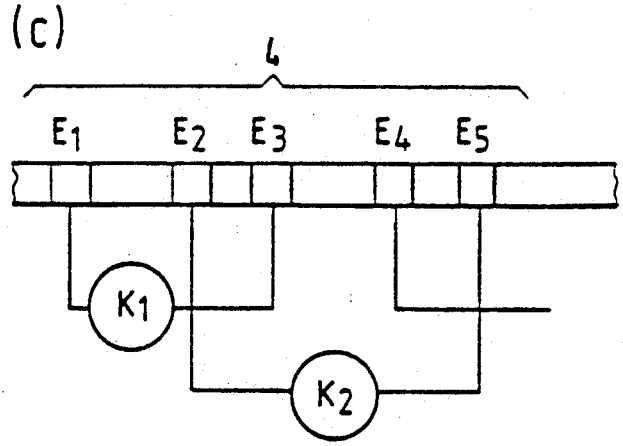

APPARATUS FOR AND METHOD OF MOTILITY AND PERISTALSIS MONITORING

This application is a continuation of Ser. No. 07/427,575, filed Oct. 23, 1989, now abandoned.

BACKGROUND OF THE INVENTION

This invention relates to medical techniques and equipment for determining motility and peristalsis in tubular organs that transport their contents. In particular, this invention relates to catheters for obtaining signals from such organs.

2. Description of the Prior Art

The primary functions of many organs includes the transport of their contents through the organ. Determination of the characteristics of that transport, i.e. motility and/or peristalsis, has important diagnostic value. The two primary conventional approaches for determination of motility and peristalsis of tubular organs are manometry and imagery.

Conventional manometry approaches measure pressure changes to characterize the contraction sequences in a narrow section of an organ to be examined. The pressure measurements be made by semiconductor pressure transducers or perfusion techniques in which pressure changes are measured in a catheter through which a constant stream of fluid flows. Organ contractions result in reduction and/or obstruction of the flow which causes measurable pressure changes.

Conventional perfusion devices require catheter tubes at least about 1 mm. diameter for each channel. Multichannel with up to eight measuring channels result in undesirably large diameter catheters. Further, the fluid introduced by the perfusion catheter into the organ may impair the organ function, particularly with long term monitoring or measurement.

Conventional imagery approaches are principally suitable for showing motility, for example in the esophagus. When such approaches are use in the intestinal area, the lack of convenient techniques for three dimensional discrimination between images results in undesirable image overlap. In addition, such techniques are relatively expensive for both acquisition of equipment and operation.

SUMMARY OF THE INVENTION

The preceding and other shortcomings of the prior art are addressed and overcome by the present invention that provides, in a first aspect, a catheter for monitoring motility and/or peristalsis in tubular organs which transport their contents, including an insulating tube sized to fit within a tubular organ, means for making multiple impedance measurements along the tube, and means responsive to characteristic points in the impedance measurements for indicating motility and/or peristalsis of the organ.

In another aspect the invention provides a method of monitoring motility and/or peristalsis in tubular organs which transport their contents, by inserting an insulating tube within a tubular organ, making multiple impedance measurements along the tube, and indicating motility and/or peristalsis of the organ in response to characteristic points in the impedance measurements.

The foregoing and additional features and advantages of this invention will become further apparent from the detailed description and accompanying drawing figures that follow. In the figures and written description, numerals indicate the various features of the invention, like numerals referring to like features throughout both the drawings and the written description.

BRIEF DESCRIPTION OF THE DRAWINGS

FIGS. 6a-6c show a series of alternate circuit configurations for connecting individual measuring channels of a catheter according to the present invention.

DETAILED DESCRIPTION OF THE PREFERRED EMBODIMENT(S)

Figure 1:
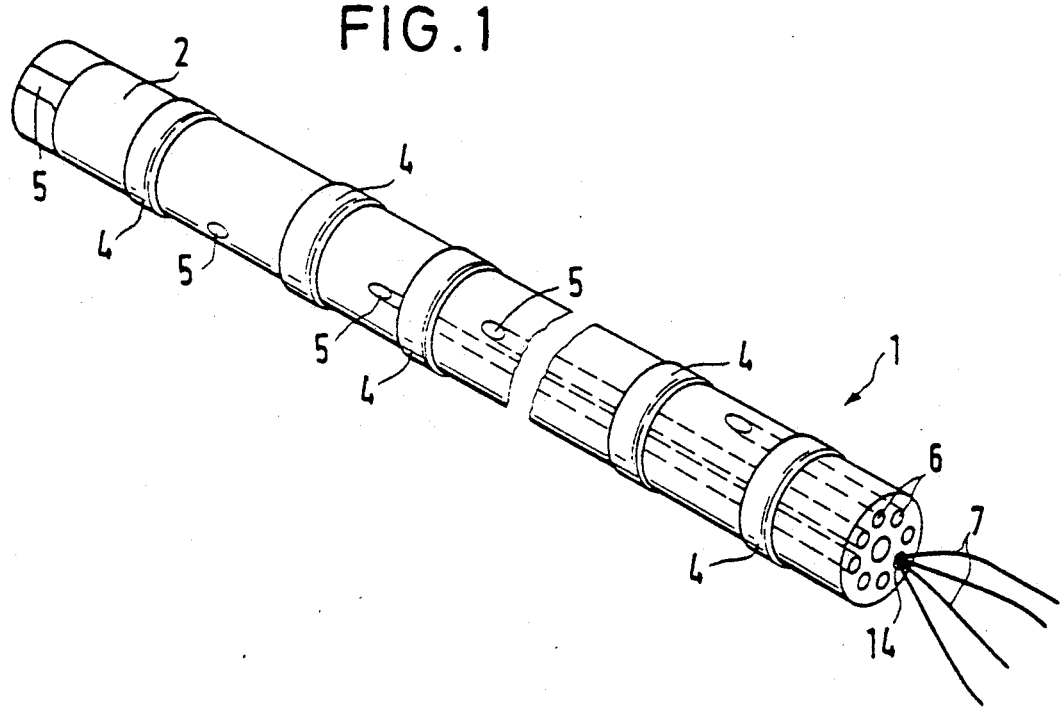
FIG. 1 shows a perspective view of a measuring section of a tubular catheter according to the present invention.

FIG. 1 is a perspective view of a measuring section of catheter 1 according to the present invention. Catheter i is used for monitoring tubular organs and particularly for obtaining electrical signals for evaluating motility and/or peristalsis in terms of space and time, namely from stationary, propulsive or repulsive waves and from contraction, spreading etc. in tubular organs that transport their contents. These electrical signals may be used as the basis for determining the characteristics, such as passage time and/or speed, and contraction frequency of the whole or specific sections of an organ. Catheter 1 may also be used for determining the dynamic resilience of tubular conveying organs.

In operation, catheter 1 is introduced into an organ, not shown, and fixed therein with regard to longitudinal displacement in a particular position. The measurement signals are obtained by simultaneous or nearly simultaneous measurements of a plurality of measuring channels.

As shown in FIG. 1, catheter 1 is constructed essentially from insulating tube 2 which may conveniently be constructed from a plastic, such as polyurethane, polyamide, polyethylene, polytetraflouroethylene, polyvinylchloride or various silicon rubber compounds. Insulating tube 2 is sized for insertion into the organ and may be flexible along its entire length or rigid along a portion of its length for convenience of use and operation.

Insulating tube 2 includes a series of internal axial longitudinal channels 6 as well as a series of annular electrodes 4 positioned around the outside of the tube. The longitudinal separation between annular electrodes 4 along insulating tube 2 depends upon the application for catheter 1, but may in a general case, be considered to be of approximately equal distances. Similarly, the longitudinal widths of annular electrodes 4 depends upon the diameter of insulating tube 2 and the application for catheter a, but may in a general case be considered to be of approximately equal widths.

Figure 2:
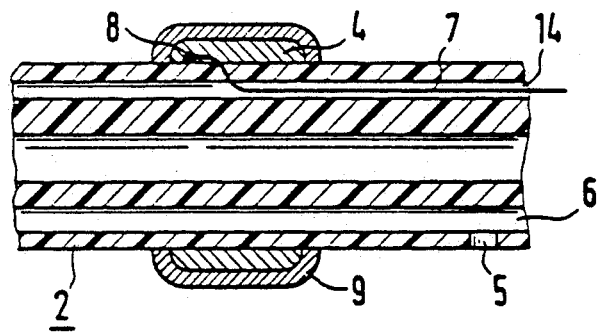
FIG. 2 shows an enlarged longitudinal cross sectional view through the measuring area of a tubular catheter according to the present invention as shown in FIG. 1.

The construction of annular electrodes 4 may be described in greater detail with reference to FIG. 2. Annular electrodes 4 are produced from flat strip material adhesively bonded to the outside of insulating tube 2. The edges of annular electrodes 4 are rounded to prevent injury to the organs and reduce resistance to insertion and removal forces. Annular electrodes 4 may conveniently be constructed from metal, electrode materials of a second type, or from conductive plastics.

Annular electrodes 4 should have low resistance and polarization voltage on their outer surface as well as provide long term stability. To enhance these characteristics, annular electrodes 4 are provided with surface coating 9 which may conveniently be a layer of silver-silver chloride.

Each annular electrode 4 is connected to the measuring instrumentation, discussed herein below With respect to the remaining figures, by electrode lead 7. Electrode lead 7 extends within a selected internal axial longitudinal channel 6, such as electrode lead channel 14, and is connected to its associated annular electrode 4 at inner contact point 8, as shown in FIG. 2.

Each annular electrode 4 forms one electrode of a measuring channel. The measuring channel is completed, as discussed below, by use of an adjacent annular electrode 4, or by means of a central body electrode which may be of any conventional type.

Catheter 1 may be provided with lumen 5, formed from an internal axial longitudinal channel 6 and an opening in the outside wall through which substances may be removed from the organ for analysis. Substances, particularly fluids, can also be introduced into the organ through lumen 5 such as contrast media or for functional stimulation of the organ. Additionally, functional stimulation can be accomplished electrically by applying the appropriate signals to annular electrodes 4. Similarly, annular electrodes 4 can be used to detect and measure electrical biosignals present in the organ.

Figure 3:
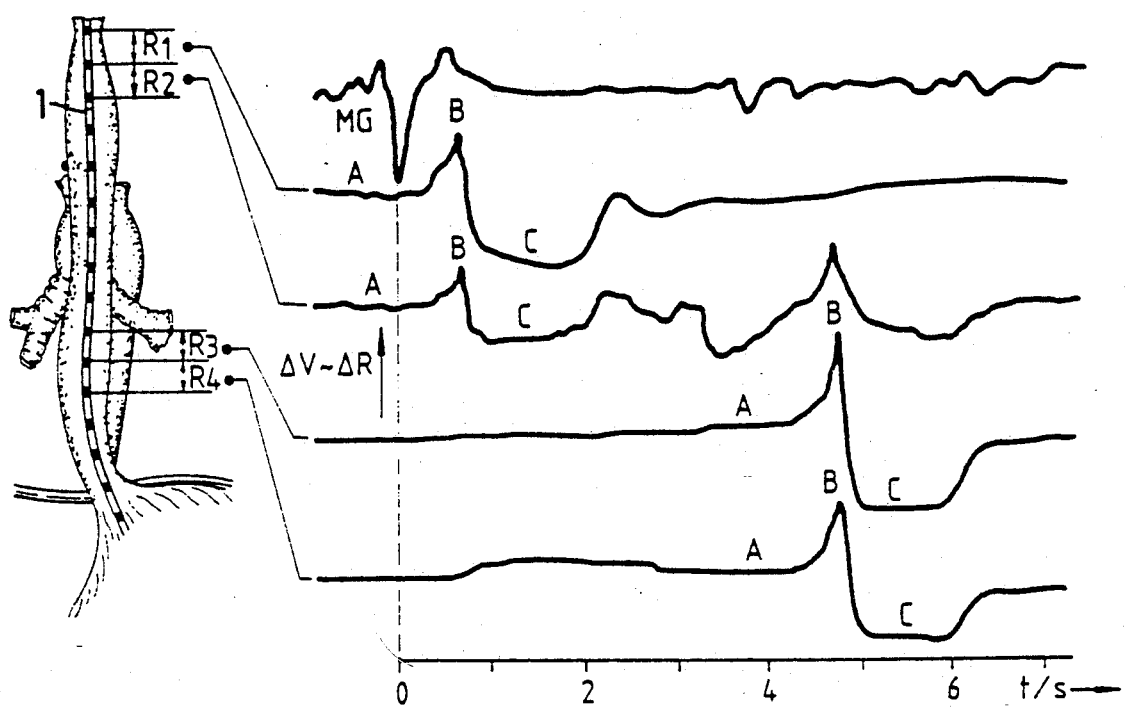
FIG. 3 illustrates the use of a tubular catheter to determine activity in an esophagus according to the present invention.
Figure 4:
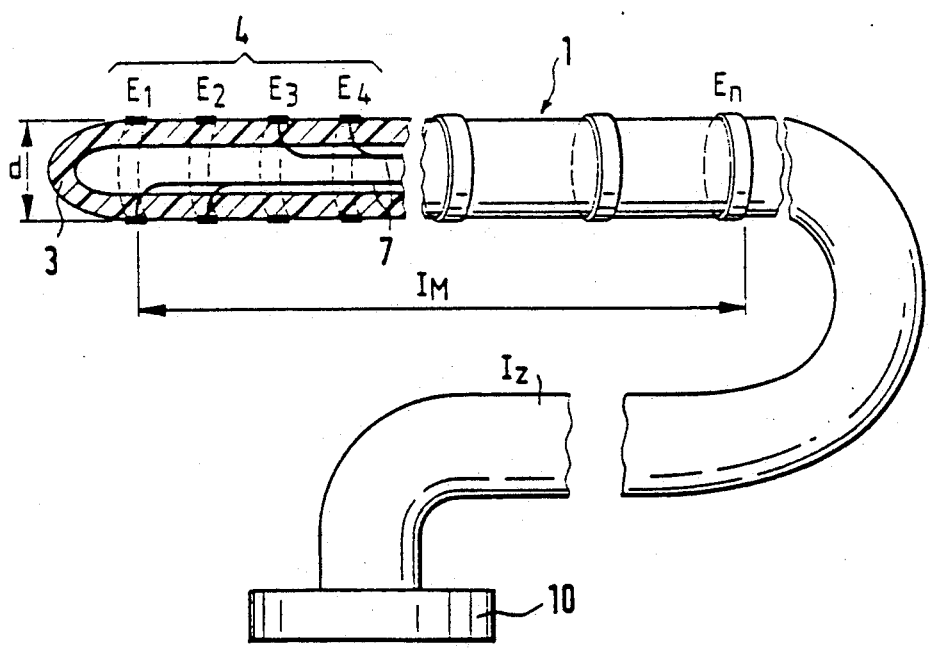
FIG. 4 shows a partially sectioned view of a preferred embodiment of a catheter according to the present invention for use as shown in FIG. 3.

FIG. 3 illustrates the use of catheter 1 to determine activity in an esophagus or other tubular organ. FIG. 4 shows a partially sectioned view of catheter 1 as shown in FIG. 3. Four specific annular electrodes 4 are designated as $E_1$, $E_2$, $E_3$ and $E_4$, respectively.

As shown in FIG. 6a, each measuring channel may be configured between two side by side annular electrodes 4 so that $E_1$ and $E_2$ form first measuring channel $K_1$, $E_2$ and $E_3$ form second measuring channel $K_2$ and $E_3$ and $E_4$ form third measuring channel $K_3$ to permit sequential longitudinal measurements.

As shown in FIG. 6b, each measuring channel may be configured between two side by side annular electrodes 4 so that $E_1$ and $E_2$ form first measuring channel $K_1$ while $E_3$ and $E_4$ form second measuring channel $K_2$ to permit sample-wise longitudinal measurements.

As shown in FIG. 6c, each measuring channel may be configured between two annular electrodes 4 that are not side by side so that $E_1$ and $E_3$ form first measuring channel $K_1$ while second measuring channel $K_2$ is formed from $E_2$ and another annular electrode 4 designated $E_5$ to permit sample-wise overlapping longitudinal measurements.

Alternatively, as noted above, each channel could be configured from an individual annular electrode 4, such as $E_1$, and a central body electrode, not shown.

Returning now to FIG. 3, MG denotes a reference channel while $R_1$, $R_2$, $R_3$ and $R_4$ represent the impedance measurements made between designated annular electrodes 4 in the Sequential fashion shown in FIG. 6a. The relative amplitudes of the voltage changes, $\Delta V$, is approximately equal to the impedance changes, $\Delta R$, and are plotted on a graph in FIG. 3 as functions of time t.

The graphs shown in this figure represent a propulsive contraction wave, characteristics points of which are indicated on the graphs as points A, B and C. The passage time and/or speed in the organ being examined can be determined from the transit times between two channels.

As shown in FIG. 4, insulating tube 2 has a well-rounded closure at front end 3 thereof and is provided with connector 10 which includes electrical connections for electrode leads 7 which extend through catheter 1. The diameter d of front end 3 may conveniently be as small a few mm. Catheter 1 may normally be flexible throughout its length, measuring portion $I_M$ may conveniently be made with varying flexibility, or even rigid, depending upon the application. The length of measuring portion $I_M$ an portion $I_z$ may typically be as long as several meters. Fluid may be inserted under pressure to an internal axial longitudinal channel 6 to provide stiffening of catheter 1 during measurement.

Catheter 1 is provided with a plurality of annular electrodes 4, some of which are identified in FIG. 4 as $E_1$, $E_2$, $E_3$ and $E_4$. All such annular electrodes 4 are connected Via electrode leads 7 to connector 10.

As shown in FIG. 1, electrode leads 7 may then be connected to an impedance measuring system including multichannel impedance transformer 12 which serves to convert the impedances to be measured into a more conveniently recorded and displayed signal form, conveniently a voltage or current signal. Signal outputs 13 of multichannel impedance transformer 12 are applied to multichannel plotting or recording device 18. Signal outputs 13 may also be processed by signal processor 17 which may conveniently include further signal processing and display systems.

In addition to the above mentioned impedance measurements, catheter 1 may be provided with one or more temperature measuring probes, not shown, along its longitudinal axis for temperature measurements Catheter 1 may also be used for receiving EMG signals which precede the mechanical contraction of an organ as well as simultaneous electrical function stimulation or excitation of the organ being examined.

Figure 5:
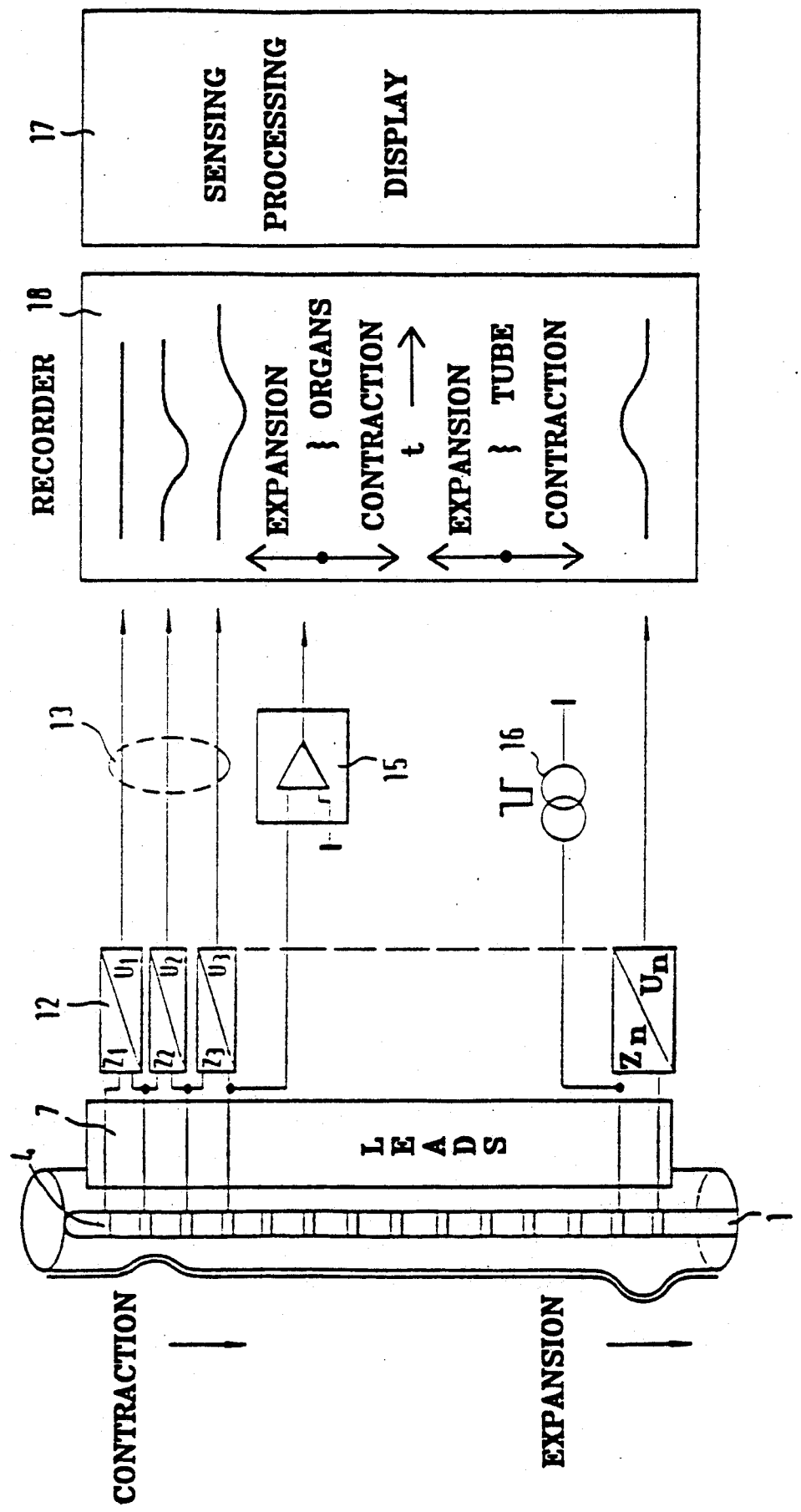
FIG. 5 illustrates in block diagram form the circuit configuration of a catheter system according to the present invention.

As shown in FIG. 5, biosignal amplifiers and/or transducers 15 can be connected to one or more electrode leads 7 for the simultaneous reception of electrical biosignals such as EMG and ECG signals. Similarly, current sources 16 can be connected to electrode leads 7 for electrical stimulation or activation of the organ being measured. In addition, pressure balloons, not shown, could be integrated within catheter a for organ stimulation.

Catheter 1 can be used to measure motility and peristaltic processes in both healthy and unhealthy organs, e.g. in the esophagus, intestines or urethra. The movement of the contents of these organs is as a rule oriented in one direction, although numerous mixed direction processes do occur, for example, in the intestines. In the intestines, the contents are moved to and fro. To accomplish this motion, the organ contractions need to be strictly synchronized. The weakening or failure of the spontaneous activity of even a small section can lead to disorders of the entire organ. In accordance with the present invention, individual sections of an organ can be readily diagnosed.

Catheter 1 may be used in technical as well as medical applications. For example, the dynamic resilience of tube walls may be measured by applying a pressure wave to stress the wall and measuring the impedance changes with catheter 1. This would be particularly useful for determination of age induced changes in the tube wall.

While this invention has been described with reference to its presently preferred embodiment, its scope is not limited thereto. Rather, such scope is only limited insofar as defined by the following set of claims and includes all equivalents thereof.

We claim as our invention:

1. Apparatus for monitoring motility and/or peristalsis in a tubular organ which transports its contents, comprising:

a catheter sized to fit within the tubular organ,
a plurality of electrodes positioned along the outside of the catheter in electrical contact with the organ at longitudinally displaced points there along,
first channel means for measuring the impedance of the organ between a pair of said electrodes;
a plurality of additional channel means for making multiple, substantially simultaneous impedance measurements between electrode pairs representing the impedance of the organ at longitudinally displaced positions along the organ; and
means for indicating the longitudinal displacement along the organ of impedance measurements made by the plurality of channel means which are characteristic of peristaltic content transport.

2. The apparatus claimed in claim 1 wherein the catheter is flexible and further comprises:

means for adjusting the flexibility of the portion of the catheter along which longitudinally displaced measurements characteristic of peristaltic content transport are made to provide stiffening of the catheter during measurement of the impedance of the organ.

3. The method of monitoring motility and/or peristalsis in a tubular organ, comprising the steps of:

making multiple, substantially simultaneous, longitudinally displaced measurements of the impedance of a peristaltic tubular organ along a catheter positioned within the organ; and
indicating the longitudinal displacement along the organ of such impedance measurements which are characteristic of peristaltic content transport in the organ.

4. The method of claim 3 further comprising the step of:

adjusting the flexibility of the portion of the catheter between the longitudinally displaced points to provide stiffening of the catheter during measurement.

5. An improved organ monitoring process of the type in which multiple channel impedance measurements are made with a multiple electrode catheter in the organ, wherein he improvement comprises the step of:

making multiple, substantially simultaneous impedance measurements representing organ impedance at longitudinally displaced positions there along; and
indicating the relative longitudinal displacement of such measurements which are characteristic of peristaltic content transport therein.

6. The method of claim 5 further comprising the following preliminary steps:

inserting the catheter in the organ, and then:
reducing the flexibility of the portion of the catheter between the longitudinally displaced positions at which such measurements are made.

7. An improved organ monitoring system of the type in which a multiple electrode catheter in the organ is used to make multiple channel impedance measurements at longitudinally displaced positions there along, wherein the improvement comprises:

means for indicating the relative longitudinal displacement along the organ of substantially simultaneous measurements which are characteristic of peristaltic content transport in he organ.

8. The system of claim 7 further comprising:

means for substantially reducing the flexibility of the portion of the catheter along which such measurements are made.

* * * * *

UNITED STATES PATENT AND TRADEMARK OFFICE
CERTIFICATE OF CORRECTION

PATENT NO. : 5,109,870
DATED : May 05, 1992
INVENTOR(S) : Jiri Silny; Günter Rau It is certified that error appears in the above-identified patent and that said Letters Patent is hereby corrected as shown below:

| | | |
|---|---|---|
| COL. 1 | LINE 8 | Below --BACKGROUND OF THE INVENTION-- insert "1. Field of the Invention"; |
| COL. 1 | LINE 25 | After --measurements-- insert "may"; |
| COL. 1 | LINE 33 | After --Multichannel-- insert "catheters"; |
| COL. 2 | LINE 21 | After --FIGS.-- replace --6a-6c-- with "6"; |
| COL. 2 | LINE 29 | Before --is-- replace --i-- with "1"; |
| COL. 2 | LINE 64 | After --catheters-- replace --a-- with "1"; |
| COL. 3 | LINE 14 | After --below-- replace --With-- with "with"; |
| COL. 3 | LINE 65 | After --the-- replace --Sequential-- with "sequential"; |
| COL. 4 | LINE 16 | After --IM-- replace --an-- with "and"; |
| COL. 4 | LINE 23 | After --connected-- replace --Via-- with "via"; |
| COL. 4 | LINE 24 | After --FIG.-- replace --1-- with "5"; |
| COL. 4 | LINE 50 | After --catheters-- replace --a-- with "1"; |

UNITED STATES PATENT AND TRADEMARK OFFICE
CERTIFICATE OF CORRECTION

PATENT NO. : 5,109,870
DATED : May 05, 1992
INVENTOR(S) : Jiri Silny; Günter Rau It is certified that error appears in the above-identified patent and that said Letters Patent is hereby corrected as shown below:

COL. 6  LINE 15  CLAIM 5  After --wherein-- replace --he-- with "the" and before --of-- replace --step-- with "steps";

COL. 6  LINE 37  CLAIM 7  After --in-- replace --he-- with "the".

Signed and Sealed this

Nineteenth Day of October, 1993

Attest:

BRUCE LEHMAN

Attesting Officer  Commissioner of Patents and Trademarks